United States Patent [19]
Zeng et al.

[11] Patent Number: 6,128,525
[45] Date of Patent: *Oct. 3, 2000

[54] APPARATUS AND METHOD TO MONITOR PHOTODYNAMIC THERAPY (PDT)

[76] Inventors: Haishan Zeng, 11786 85B Avenue, Delta, B. C., Canada, V4C 2W2; Harvey Lui, 3415 West 11th Avenue, Vancouver, B. C., Canada, V6R 2K1; Calum MacAulay, 5791 Prince Albert Street, Vancouver, B. C., Canada, V5W 3E1; Branko Palcic, 3758 Quesnel Drive, Vancouver, B. C., Canada, V6L 2W8; David I. McLean, 1246 West 26th Avenue, Vancouver, B. C., Canada, V6H 2A9

[*] Notice: This patent issued on a continued prosecution application filed under 37 CFR 1.53(d), and is subject to the twenty year patent term provisions of 35 U.S.C. 154(a)(2).

[21] Appl. No.: 08/901,999

[22] Filed: Jul. 29, 1997

[51] Int. Cl.⁷ ...................................................... A61B 6/00
[52] U.S. Cl. .......................................... 600/476; 600/317
[58] Field of Search .................................. 372/21, 22, 23; 606/10, 16, 14; 382/133, 191; 600/476, 317

[56] References Cited

U.S. PATENT DOCUMENTS

| | | |
|---|---|---|
| 4,957,114 | 9/1990 | Zeng et al. . |
| 5,028,594 | 7/1991 | Carson . |
| 5,151,909 | 9/1992 | Davenport et al. ........................ 372/22 |
| 5,284,831 | 2/1994 | Kahl et al. . |
| 5,445,608 | 8/1995 | Chen et al. . |
| 5,485,530 | 1/1996 | Lakowicz et al. ....................... 382/191 |
| 5,514,127 | 5/1996 | Shanks ..................... 606/10 |
| 5,522,868 | 6/1996 | Buckley et al. . |
| 5,533,508 | 7/1996 | Doiron . |
| 5,556,612 | 9/1996 | Anderson et al. . |
| 5,572,996 | 11/1996 | Doiron et al. . |
| 5,701,902 | 12/1997 | Vari et al. . |
| 5,705,518 | 1/1998 | Richter et al. . |

OTHER PUBLICATIONS

Anna M. Richter; Barbara Kelly; Jack Chow; Daniel J. Lui; G.H. Towers; David Dolphin and Julia G. Levy—Preliminary Studies on a More Effective Phototoxic Agent than Hematoporphyrin—Dec. 1987 JNCL vol. 79, No. 6, pp. 1327–1332.

A. M. Richter; E. Waterfield; A.K. Jain; B. Allison; E.D. Sterberg; D. Dolphin and J.G. Levy—Photosensitising potency of structural analogues of benziporphyrin derivative (BPD) in a mouse tumour model—1991—Macmillan Press Ltd., pp. 87–93.

Haishan Zeng; Calum MacAulay; David I. McLean; Harvey Lui; Branko Palcic—Miniature spectrometer and multispectral imager as a potential diagnostic aid in dermatology—SPIE vol. 2387—1995—pp. 57–61.

(List continued on next page.)

*Primary Examiner*—Marvin M. Lateef
*Assistant Examiner*—Ali M. Imam
*Attorney, Agent, or Firm*—Fulwider Patton Lee & Utecht, LLP

[57] ABSTRACT

A method and apparatus for controlling the dosimetry of a photodynamic therapy that involves exposing a site to be treated to treatment light in order to generate toxic products at the site and other photoproducts. Often a photosensitizer drug is administered to the patient prior to treatment or the therapy relies on the presence of endogenous photosensitizers. The method comprises the steps of selecting a photoproduct having an identifying characteristic, which can be a fluorescence peak, and monitoring the photoproduct using the identifying characteristic (e.g. fluorescence) to determine the level of the photoproduct being generated. The photodynamic therapy is then terminated when the photoproduct being monitored reaches a predetermined level. The method allows for safe treatment of a site using photodynamic therapy and ensures that overexposure to treatment light leading to damage of normal tissue or underexposure leading to ineffective treatment of the lesion does not occur. Apparatus for automatically carrying out the method is also provided.

2 Claims, 3 Drawing Sheets

OTHER PUBLICATIONS

Haishan Zeng; Calum MacAulay; David I. McLean; Harvey Lui; Branko Palcic—Update on fluorescence spectroscopy studies of diseasead skin—Conference: Lasers in Dermatology and Plastic Surgery, BiOS '96, Jan. 27–Feb. 2, 1996—SPIE Code #2671E–42—pp. 1–3.

Haishan Zeng; Calum MacAulay; David I. McLean; Harvey Lui; Branko Palcic—European BioMedical Optics—BiOS Europe '95 Barcelona, Spain, Sep. 12–16, 1995 (p. 145)—Optical spectroscopy studies of diseased skin.

Haishan Zeng; Calum MacAulay; David I. McLean; Harvey Lui; Branko Palcic—Non–invasive, Bedside Autoflourescence Spectroscopy of Benign and Malignant Skin Lesions—Fourth Meeting of the Western Canadian Society for Clinical and Investigative Dermatology, Jasper, AB, Mar. 24–26, 1995.

Haishan Zeng; Calum MacAulay; David I. McLean; Harvey Lui; Branko Palcic—Quantitative Analysis of Laser Induced Autofluoresence Spectra of Diseased Skin—Photonics China '96—Lasers in Medicine and Dentistry; Diagnostics and Treatment—Beijing, China, Nov. 4–7, 1996.

Haishan Zeng; Calum MacAulay; David I. McLean; Harvey Lui; Branko Palcic—Update on Fluorescence Spectroscopy Studies of Diseased Skin—SPIE BiOS '96—San Jose, CA—Jan. 27–Feb. 2, 1996, Paper 2671E–42, Session 8, p. 12.

Haishan Zeng; Calum MacAulay; David I. McLean; Harvey Lui; Branko Palcic—Ratio Analysis of Reflectance and Fluorescence Spectra of Diseased Skin—$24^{th}$ Annual Meeting of the American Society for Photobiology, Atlanta, Georgia—Jun. 15–20, 1996.

Haishan Zeng; Calum MacAulay; David I. McLean; Harvey Lui; Branko Palcic—Optical Spectroscopy as a Potential Diagnostic Aid for Dermatology—Clinical Dermatology 2000—An International Congress, Vancouver, B.C., May 28–31, 1996—Programme and Abstracts, Abstract 584, p. 176.

H. Lui, et al.; "In Vivo Fluorescence Spectroscopy Monitoring of BPD Verteporfin Concentration Changes in Skin Tissue During Photodynamic Therapy of Skin Cancer", The First Joint Meeting of the Japanese and Canadian Societies for Investigative Dermatology, Whistler, BC, May 28–31, 1996, IN: Journal of Dermatological Science 12, p. 87, Abstract 30 (1996).

H. Lui, et al.; "Penetration Depth of Topical BPD Verteporfin in Rabbit Skin Determined by Microspectrophotometer Measurements", The First Joint Meeting of the Japanese and Canadian Societies for Investigative Dermatology, Whistler, BC, May 28–31, 1996, IN: Journal of Dermatological Science 12, p. 86, Abstract 22 (1996).

APPARATUS AND METHOD TO MONITOR PHOTODYNAMIC THERAPY (PDT)

FIELD OF THE INVENTION

This invention relates to method and apparatus for monitoring treatment of a patient undergoing photodynamic therapy in order to determine when the correct light and/or drug dosage is reached.

BACKGROUND OF THE INVENTION

Photodynamic therapy (PDT) is a method for treating cancers and other diseased tissues. In photodynamic therapy, a photosensitizer drug is generally administered to the patient and the disease site to be treated is then exposed to light, however, in the presence of endogenous photosensitizers, the administration of a photosensitizer drug may not be absolutely necessary for performing PDT. If the site is internal, it is necessary to expose the site using an endoscopic probe that contains a fiber optic cable. Once exposed to light, the photosensitizer drug (or endogenous photosensitizer) is excited and interacts with molecular oxygen to create toxic species that include singlet oxygen. Singlet oxygen reacts with the tissues and causes cell damage which kills or alters the cells. A significant limitation of photodynamic therapy is that healthy tissue as well as diseased or abnormal tissue is affected. Too much illumination will damage normal tissue while insufficient illumination will result in inadequate treatment.

Therefore, it is important that the various factors affecting the therapy be carefully controlled to ensure optimal treatment. Factors affecting photodynamic therapy include the photosensitizer drug dose, or the quantity of endogenous photosensitizers present, the light dose, pharmacokinetics of the drug, distribution of the drug in the tissue, distribution of the light in the tissue, and oxygen supply. All of the above factors are subject to biological variations in individual patients as well as variations in the disease and the specific disease site. The dosimetry parameters derived from in vitro measurements, animal studies, theoretical modelling, and prior experience with other patients may not be optimal for any given patient. At present, there is no effective method in clinical practice for determining when the treatment site has received its optimal light exposure.

SUMMARY OF THE INVENTION

In PDT treatment, photoproducts are generated from the photosensitizer drug or endogenous photosensitizers as a result of light exposure, and are believed to be proportional to the light-photosensitizer interactions occurring in the tissue. By virtue of having discovered that photoproducts generated during photodynamic therapy show unique fluorescence peaks, applicants have developed a method and apparatus to monitor the progress of photodynamic therapy by monitoring the level of a photoproduct. When the photoproduct reaches a predetermined level, therapy is stopped.

Accordingly, the present invention provides a method for controlling the dosimetry of photodynamic therapy (PDT) that involves exposing a site to be treated to treatment light in order to generate toxic products at the site and other photoproducts, comprising the steps of:

selecting at least one photoproduct such that the photoproduct has an identifying characteristic and such that the level of the photoproduct being generated is proportional to the toxic effect of the PDT therapy;

monitoring the at least one photoproduct using the identifying characteristic to determine the level of the photoproduct being generated; and terminating the photodynamic therapy when the at least one photoproduct being monitored reaches a predetermined level.

Preferably, the method uses the peak in the fluorescence spectrum of a photoproduct as the identifying characteristic. The fluorescence spectrum is captured and a ratio spectrum technique is used to improve the signal to noise ratio to enhance the peak of the spectrum. The level of photoproduct is determined and once the level reaches a predetermined threshold, the therapy is stopped by shutting off the treatment light or removing the PDT drug.

In addition, the method of the present invention uses fluorescence imaging to monitor treatment by taking into account the distribution of the photoproducts over the treatment site. A light valve can be controlled to regulate distribution of the treatment light to only those areas of the treatment site where lack of photoproduct build up indicates that more treatment is required.

In a further aspect, the present invention provides apparatus for controlling the dosimetry of photodynamic therapy that involves exposing a site to be treated to treatment light from a treatment light source in order to generate toxic products at the site and other photoproducts, at least one of the photoproducts being generated at levels proportional to the toxic effect of the PDT therapy and having an identifying characteristic, comprising:

means for monitoring the identifying characteristic of the at least one photoproduct to determine the level of the photoproduct being generated; and means for terminating the photodynamic therapy when the at least one photoproduct being monitored reaches a predetermined level.

Preferably, the apparatus is automatically controlled by a computer that automates the therapy procedure.

BRIEF DESCRIPTION OF THE DRAWINGS

Aspects of the present invention are illustrated, merely by way of example, in the accompanying drawings in which.

DESCRIPTION OF THE PREFERRED EMBODIMENTS

Figure 1:
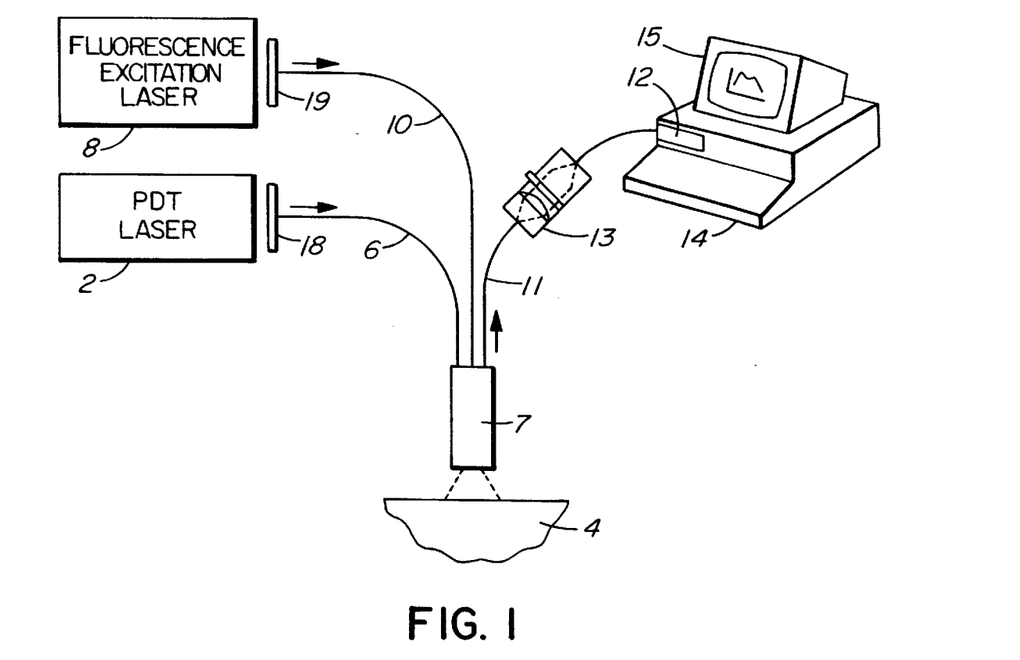
FIG. 1 is a schematic view of a first embodiment of the apparatus of the present invention that uses the fluorescence spectrum.

Referring to FIG. 1, there is shown schematically a preferred embodiment of the apparatus of the present invention used for controlling the dosimetry of photodynamic therapy. In order to administer photodynamic therapy, there is provided a light source 2 that illuminates a treatment site 4 through an optic fibre 6.

As explained above, when the treatment site is illuminated by light source 2, the photosensitizer drug or endogenous photosensitizers causes toxic products and other photoproducts to develop in the tissues. It is preferable, that a photosensitizer drug be administered to the patient prior to treatment. By way of an example, the applicants have discovered that when the drug BPD verteporfin (BPD) is used as the photosensitizer, one of the generated photoproducts has a unique identifying characteristic comprising a peak at 650 nm in the fluorescence spectrum that can be monitored to track the level of photoproducts at treatment site 4 such that once a pre-set photoproduct level is reached, the therapy is stopped.

Means for monitoring the spectrum peak are provided comprising a light source 8 for generating excitation light, means for delivering the excitation light to the site to be treated in the form of optical fibre 10, means for capturing the resulting fluorescence spectrum in the form of spectrometer 12, and processing means for analysing the captured fluorescence spectrum. A computer 14 is provided to control the various components.

Preferably, optical fibres 10 and 6 are incorporated into probe 7. In addition, a third optical fibre 11 is also included in probe 7 to transmit the fluorescence light to spectrometer 12. A long wave pass (LP) filter 13 can be installed in fibre 11 to filter out the reflected excitation light for fluorescence spectral analysis. Probe 7 holds the three fibers (6, 10, 11) together and can be directly used for skin treatment. It is also compact enough so that it can be inserted through the biopsy channel of an endoscope to treat internal organs such as the respiratory and gastrointestinal tracts.

Alternatively, light source 2 can be an LED (light emitting diodes) panel or a filtered lamp system with fiber bundle light guide or liquid light guide, in which case, the treatment site is illuminated directly and fiber 6 is not needed. Then, probe 7 will only hold fiber 10 and 11 for fluorescence spectral monitoring.

Spectrometer 12 communicates with computer 14 and includes a display monitor 15 to view spectral graphs generated in real time. Computer 14 runs a computer program that analyses the fluorescence spectrum in real time in order to isolate the spectral peak of the photoproducts and determine the level of the photoproduct.

Figure 2:
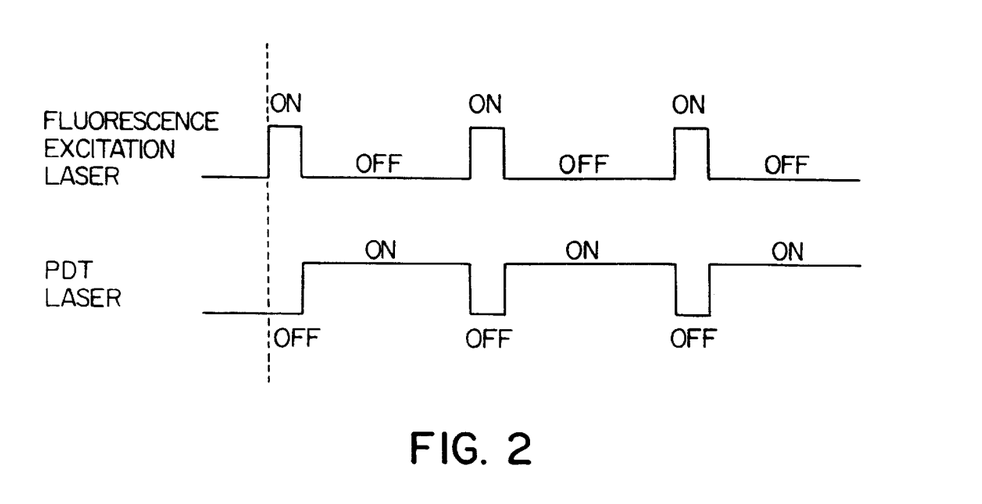
FIG. 2 is a timing diagram of a preferred illumination sequence of the treatment site using a treatment light and a fluorescence excitation light.

Means to alternate illumination of the site by the treatment light and the excitation light are provided in the form of electrical shutter mechanisms 18 and 19. The shutters, both under computer control, are provided to control exposure of the treatment site 4 to light. During the photodynamic therapy, for the majority of time site 4 is exposed to treatment light emitted by laser 2 by opening shutter 18 and closing shutter 19 to active the photosensitizer drug. At set intervals, shutter 19 is opened and shutter 18 is closed so that light from excitation laser 8 is transmitted to the site in order to generate and capture the fluorescence spectrum of the site. FIG. 2 is a timing diagram showing the lighting scheme described above. Note that whenever treatment light source 2 is off (shutter 18 is closed), excitation light source 8 is on (shutter 19 is open), and vice versa.

Shutter 18 also acts as the means for terminating the photodynamic therapy in response to a control signal from computer 14 when the level of the photoproduct reaches the pre-set level.

Alternatively, a more expensive gating spectrometer 12 and pulsed laser as excitation light source 8 could be used to monitor the fluorescence spectra. In this case, the treatment light source 2 can remain on throughout the entire exposure procedure.

Figure 3A:
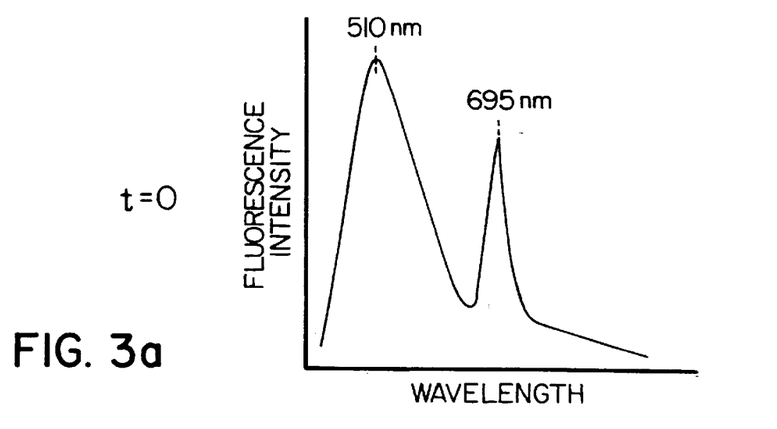
FIGS. 3a, 3b and 3c are spectrum graphs showing the original fluorescence spectra at times t=0, t=T and the ratio spectra, respectively, according to the analysis technique of the present invention.

In operation, the apparatus described in FIG. 1 is used in the following manner:

Initially (t=0), a fluorescence spectrum is obtained immediately before the PDT treatment light irradiation begins. The captured spectrum (FIG. 3a) provides a baseline signal that takes into account the autofluorescence emissions of the site and the fluorescence from the photosensitizer drug. Then, by operation of shutters 18 and 19, the site is alternately exposed to treatment light and excitation light and the apparatus is used to monitor the level of the photoproduct that is generated.

Figure 3B:
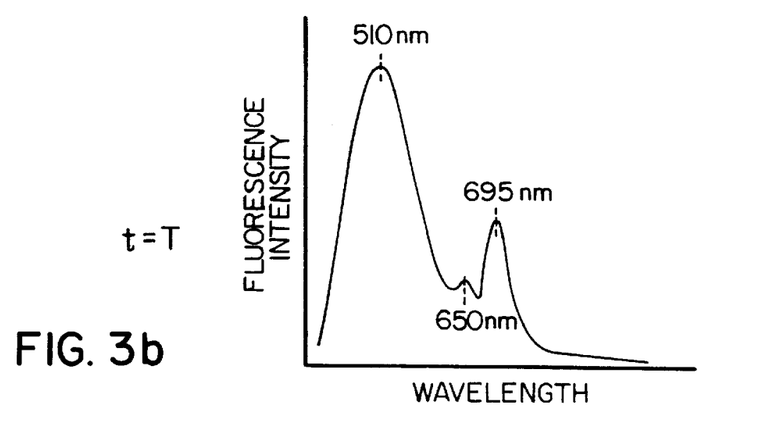

Whenever the site is exposed to excitation light, the light collected for spectral analysis includes autofluorescence emissions from the tissue, fluorescence emissions from the photosensitizer drug or endogenous photosensitizers which decrease as the treatment progresses due to photobleaching, and fluorescence emissions from the newly generated photoproducts. This light is collected by optical fibre 11 and transmitted to spectrometer 12 for capture and analysis to determine the level of photoproduct. At time T, the spectrum is illustrated in FIG. 3b.

Figure 3C:
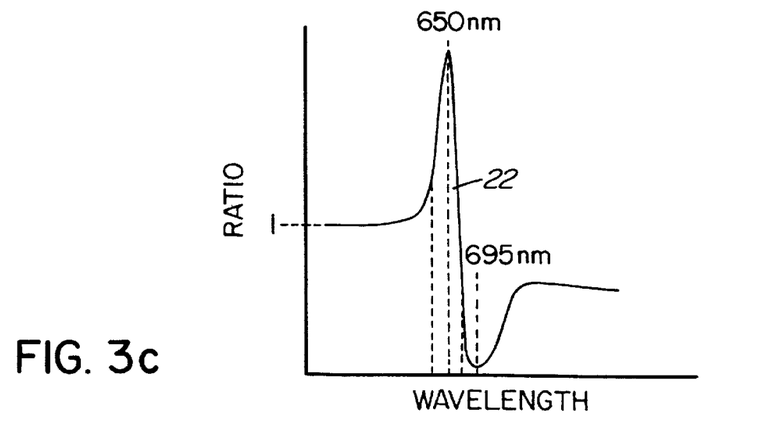

Analysis of the fluorescence spectrum is performed by a program running in computer 14. The initial fluorescence spectrum obtained prior to commencement of the PDT treatment light irradiation is stored by the computer. In a ratio spectrum technique developed to extract the photoproduct fluorescence signal, the fluorescence spectrum captured at each interval is divided by the initial fluorescence spectrum. The result is a ratio spectrum as shown in FIG. 3c which is a plot of wavelength on the x-axis and the intensity ratio on the y-axis. The illustrated plot is a general representation of the ratio spectrum for the photosensitizer drug BPD. This particular drug can be activated using 690 nm light and has a photoproduct fluorescence peak at 650 nm when excited with a 442 nm He-Cd laser. This peak is not nearly so obvious on a non-ratio spectrum FIG. 3b. At the lower wavelength end, the ratio is close to 1 since the lower wavelength autofluorescence spectral signal of the tissue does not change much. At higher wavelengths, the trough at 695 nm is seen due to photobleaching of the BPD photosensitizer drug. For longer wavelengths, the ratio tends to a stable value of less than 1 since the longer wavelength signal has a contribution from the BPD fluorescence and the BPD has been photobleached during photodynamic therapy. The photobleaching changes on the fluorescence spectra are not suitable for dosimetry because they can be offset by photosensitizer re-accumulation.

The ratio spectra collected during each illumination by excitation light source 8 are further processed by calculating in real time the integrated spectral intensity at a wavelength band adjacent the peak in the fluorescence spectrum which is shown as the shaded area 22 in FIG. 3c. When this integrated intensity reaches a pre-set threshold, the computer 14 will cause shutter 18 to close to prevent further exposure of the treatment site 4 to the treatment light, thereby terminating the photodynamic therapy.

In an additional embodiment, the method and apparatus of the present invention use fluorescence imaging to monitor treatment to take into account the spatial distribution of the photoproducts over the lesion being treated.

Figure 4:
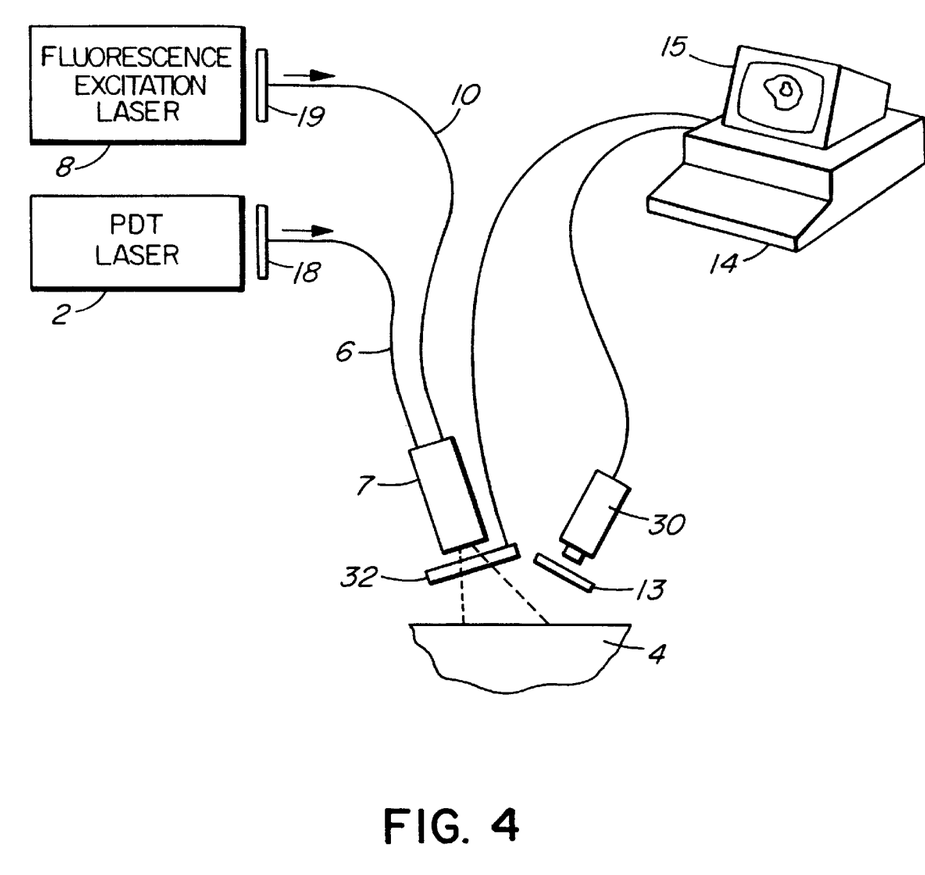
FIG. 4 is a schematic view of an alternative embodiment of the apparatus of the present invention that uses fluorescence imaging.

Referring to FIG. 4, there is shown apparatus for monitoring PDT treatment using fluorescence imaging. This arrangement is similar to the apparatus of FIG. 1 except CCD camera 30 is used to capture a fluorescence image of the treatment site rather than spectrometer 12 capturing a fluorescence spectrum. As well, a light valve 32 is incorporated into the path of the treatment light so that the distribution of the light over the site can be regulated as will be explained below. The CCD camera can view the PDT site directly or through a coherent imaging optical fibre bundle of an endoscope.

In a manner similar to the apparatus of FIG. 1, the apparatus of FIG. 4 is used to capture fluorescence images at CCD camera 30. The images are comprised of a large number of discrete picture elements or pixels. The captured images are analysed by measuring a first fluorescence image over a relatively narrow wavelength band around the peak in the fluorescence spectrum of the photoproduct and by measuring a second fluorescence image over a wavelength band adjacent the peak and remote from any other PDT fluorescence peaks. By way of example, when BPD is used as the photosensitizer and light of 442 nm is used as the excitation wavelength, the second image is measured using light in the range of 510 nm which represents the autofluorescence signal of the tissue. This signal does not change much during PDT treatment. The first image is measured using light in the range of 650 nm which represents the peak signal from the photoproduct. The second image can also be a reflectance image of the excitation light since reflectance does not change much during PDT treatment.

The first and second images are processed in computer 14 to generate a ratio image by dividing the second image by the first image. The first image serves to calibrate the second image for possible differences in distance from each pixel to the CCD camera imaging system and the possible non-uniform intensity distribution of the excitation light. This ratio image, $R(x,y)$, is obtained before, $R_o(x,y)$, and during, $R_T(x,y)$, PDT treatment at predetermined time intervals. Normalising the ratio images at times T after the start of PDT treatment to the ratio image at time T=0 before PDT treatment gives a map of the photoproduct distribution over the treatment site. Thus, the photoproduct distribution over the treatment site at time T can be expressed as $R_T(x,y)/R_o(x,y)$. Based on the photoproduct distribution determined by normalization of the ratio images, computer 14 sends control signals to light valve 32 to modulate the intensity of the treatment light according to the spatial distribution of the photoproducts so that uniform treatment effects can be obtained over the whole treatment site thereby further optimising the effects of the PDT treatment.

The modulation of the treatment light at the site is accomplished by light valve 32 under the control of computer 14. Light valve 32 is either a liquid crystal spatial light modulator (LCD-SLM, Hamamatsu Photonics Corp.) or a digital micromirror device (DMD™, Texas Instruments Inc.).

The LCD-SLM uses a liquid crystal layer to act as a light valve. The transmittance of each pixel can be controlled by an electrical signal from computer 14. The 2-D light intensity modulation can be controlled by a video image signal which, in this application, would be a representation of the photoproduct 2-D distribution.

A DMD can be described simply as a semiconductor light switch. Thousands of tiny, square, 16×16 $\mu$m mirrors, fabricated on hinges atop a static random access memory make up a DMD. Each mirror is capable of switching a pixel of light. The hinges allow the mirror to tilt between two states, +10 degrees for "on" or −10 degrees for "off". The DMD can be addressed by a digital image signal to control how long a mirror stays on and off. Therefore, if a uniform treatment light beam illuminates the DMD, the 2-D photoproducts distribution image is used to spatially modulate the DMD, then the reflected light beam reaching the tissue being treated will be spatially modulated by the 2-D photoproducts distribution.

The method and apparatus of the present invention measures the biological effect of the photodynamic therapy treatment and avoids the problem of biological variation from patient to patient and from disease site to disease site. Even if the same amount of photosensitizer drug per kilogram of body weight is injected into different patients, the drug accumulation at disease sites in different patients may vary. The drug accumulation at different sites in the same patient may also be different. Conventional dosimetry sets substantially the same treatment light dosage for all disease sites and for different patients resulting often in "over treatment" or "under treatment" of the disease site. By using the method and apparatus of the present invention, an appropriate treatment light dosage is given that is sufficient to effectively treat a particular disease site by tracking the actual biological effect of the treatment by monitoring the photoproducts. It is necessary to establish the correct predetermined value of the photoproduct so that optimal treatment will be achieved.

Although the present invention has been described in some detail by way of example for purposes of clarity and understanding, it will be apparent that certain changes and modifications may be practised within the scope of the appended claims.

We claim:

1. A method for controlling the dosimetry of photodynamic therapy (PDT) that involves exposing a site to be treated to treatment light in order to generate toxic products at the site and other photoproducts, comprising the steps of:

selecting at least one photoproduct such that the photoproduct has an identifying characteristic comprising a peak in a fluorescence spectrum of the at least one photoproduct and such that the level of the photoproduct being generated is proportional to the toxic effect of the PDT therapy;

monitoring the at least one photoproduct using the identifying characteristic to determine the level of the photoproduct being generated, the monitoring performed by a) exposing the treatment site to an excitation light; b) capturing resulting fluorescence images by i) capturing a first fluorescence image over a narrow wavelength band around the peak in the fluorescence spectrum of the photoproduct; ii) capturing a second fluorescence image over a wavelength band adjacent to the photoproduct peak and remote from any other PDT fluorescence peaks; and, iii) dividing the fluorescence image captured in step i) by the fluorescence image captured in step b) to obtain a ratio image; c) analysing the captured fluorescence images to determine the level of the at least one photoproduct by i) obtaining the ratio image of the site before exposing the site to treatment light; and, ii) dividing each ratio image acquired during PDT treatment by the ratio image of step a) to determine the distribution at the site of the levels of the at least one photoproduct; d) repeating steps a), b), and c) at set intervals;

terminating the photodynamic therapy when the at least one photoproduct being monitored reaches a predetermined level; and, modifying the distribution of the treatment light at the site based on the distribution at the site of the levels of the at least one photoproduct by controlling a light valve in the path of the treatment light to regulate how much treatment light will be received by different areas of the treatment site, wherein the light valve is a digital micromirror device.

2. Apparatus for controlling the dosimetry of photodynamic therapy that involves exposing a site to be treated to treatment light from a treatment light source in order to generate toxic products at the site and other photoproducts, at least one of the photoproducts being generated at levels proportional to the toxic effect of the PDT therapy and having an identifying characteristic comprising a peak in a fluorescence spectrum of the at least one photoproduct, comprising:

means for monitoring the identifying characteristic of the at least one photoproduct to determine the level of the photoproduct being generated, the means for monitoring comprising a light source for generating excitation light, means for delivering the excitation light to the site to be treated, means for capturing resulting fluorescence images comprising a CCD camera, and processing means for analysing the captured fluorescence images to determine the level of the at least one photoproduct wherein the processing means comprises a computer program to analyse the fluorescence images by generating a ratio image at predetermined intervals during PDT treatment according to the following steps: a) measuring a first fluorescence image over a narrow wavelength band around the peak in the fluorescence spectrum of the photoproduct, b) measuring a second fluorescence image over a wavelength band adjacent to the photoproduct peak and remote form any other PDT fluorescence peaks, c) dividing the fluorescence image captured in step a) by the fluorescence image captured in step b) to obtain a ratio image of the treatment site, and d) dividing the ratio image of the site acquired at a predetermined interval by a ratio image of the site before exposure to treatment light to determine the distribution at the site of the levels of the at least one photoproduct;

means for terminating the photodynamic therapy when the at least one photoproduct being monitored reaches a predetermined level;

a computer to control the means for monitoring and the means for terminating the photodynamic therapy; and a light valve positioned in the path of the treatment light to regulate the areas of the site that receive treatment light in response to control signals from the computer based on the distribution at the site of the levels of the at least one photoproduct, wherein the light valve is a digital micromirror device.

\* \* \* \* \*

UNITED STATES PATENT AND TRADEMARK OFFICE
CERTIFICATE OF CORRECTION

PATENT NO. : 6,128,525
DATED : October 3, 2000
INVENTOR(S) : Haishan Zeng, et al.

It is certified that error appears in the above-identified patent and that said Letters Patent is hereby corrected as shown below:

Title page,
Under "OTHER PUBLICATIONS", add the following ten articles:

-- Amit, I. et al., "Photoproduct Formation from a Zinc Benzochlorin Iminium Salt Detected by Fluorescence Microscopy," *Photochemistry and Photobiology B: Biology* 69(6):700-702, 1999.

Castell, Jose V. et al., "Photodynamic Lipid Peroxidation by the Photosensitizing Nonsteroidal Anti-inflammatory Drugs Suprofen and Tiaprofenic Acid," *Photochemistry and Photobiology* 59(1):35-39, 1994.

Dickson, E.F. Gudgin and Pottier, R.H., "On the role of protoporphyrin IX photoproducts in photodynamic therapy," *J. Photochemistry and Photobiology B: Biology* 29:91-93, 1995.

Gillies, R. et al., "Special characterization of the benzoporphyrin derivative monoacid ring-A photoproduct formed in fetal calf solutions during irradiation with 694 nm continuous-wave radiation," *J. Photochemistry and Photobiology B:Biology* 33:87-90, 1996.

Konig, K. et al., "Variation in the fluorescence decay properties of haematoporphyrin derivative during its conversion to photoproducts," *J. Photochemistry and Photobiology B: Biol.* 8:103-111, 1990.

Konig et al., "In vivo photoproduct formation during PDT with ALA-induced endogenous porphyrins," *J. Photochemistry and Photobiology B: Biol.* 18(2-3):287-290, 1993.

Orth, K. et al., "Photodynamic therapy of experimental colonic tumours with 5-amivolevulinic-acid-induced endogenous porphyrins," *J. Cancer Res. Clin. Oncol.* 120:657-661, 1994.

Rotomskis, R. et al., Spectroscopic studies of photobleaching and photoproduct formation of porphyrins used in tumour therapy," *J. Photochemistry and Photobiology B: Biology* 33:61-67, 1996.

Robinson, Dominic J. et al., "Fluorescence Photobleaching of ALA-induced Protoporphyrin IX during Photodynamic Therapy of Normal Hairless Mouse Skin: The Effect of Light Does and Irradiance and the Resulting Biological Effect," *Photochemistry and Photobiology* 67(1):140-149, 1998.

UNITED STATES PATENT AND TRADEMARK OFFICE
CERTIFICATE OF CORRECTION

PATENT NO. : 6,128,525
DATED : October 3, 2000
INVENTOR(S) : Haishan Zeng, et al.

It is certified that error appears in the above-identified patent and that said Letters Patent is hereby corrected as shown below:

van Leengoed, H.L.L.M. et al., "In vivo fluorescence and photodynamic activity of zinc phthalocyanine administered in liposomes," *British J. Cancer* 69(5):840-845, 1994. --.

Signed and Sealed this

Thirteenth Day of November, 2001

Attest:

*Nicholas P. Godici*

NICHOLAS P. GODICI
*Attesting Officer*   *Acting Director of the United States Patent and Trademark Office*